(12) United States Patent
Yin et al.

(10) Patent No.: US 7,378,090 B2
(45) Date of Patent: May 27, 2008

(54) ALLEVIATION OF THE MEMORY DEFICITS AND MEMORY COMPONENTS OF PSYCHIATRIC DYSFUNCTIONS BY ALTERING ATYPICAL PKM ACTIVITY

(75) Inventors: Jerry C. P. Yin, Huntington, NY (US); Eric A. Drier, Huntington, NY (US); Todd C. Sacktor, Yonkers, NY (US)

(73) Assignees: The Research Foundation of State University of New York, Albany, NY (US); Cold Spring Harbor Laboratory, Cold Spring Harbor, NY (US)

( * ) Notice: Subject to any disclaimer, the term of this patent is extended or adjusted under 35 U.S.C. 154(b) by 109 days.

(21) Appl. No.: 10/135,183

(22) Filed: Apr. 29, 2002

(65) Prior Publication Data

US 2003/0068310 A1    Apr. 10, 2003

Related U.S. Application Data

(60) Provisional application No. 60/326,948, filed on Oct. 4, 2001, provisional application No. 60/287,165, filed on Apr. 27, 2001.

(51) Int. Cl.
*A01K 67/027* (2006.01)
*G01N 33/567* (2006.01)
*A61K 39/395* (2006.01)

(52) U.S. Cl. ............ 424/94.5; 424/94.1; 435/7.2; 435/15; 530/388.26

(58) Field of Classification Search ........... 424/94.1, 424/94.5; 435/7.2; 530/388.26
See application file for complete search history.

(56) References Cited

U.S. PATENT DOCUMENTS

| | | |
|---|---|---|
| 5,681,747 A | 10/1997 | Boggs et al. |
| 5,786,362 A | 7/1998 | Krongrad |
| 5,882,927 A | 3/1999 | Bennett et al. |
| 5,885,970 A | 3/1999 | Bennett et al. |
| 5,916,807 A | 6/1999 | Bennett et al. |
| 5,922,686 A | 7/1999 | Bennett et al. |
| 5,959,096 A | 9/1999 | Bennett et al. |
| 2003/0129179 A1* | 7/2003 | Sacktor ............... 424/94.5 |

FOREIGN PATENT DOCUMENTS

| | | | |
|---|---|---|---|
| WO | WO 93/20101 A1 | 10/1993 | |
| WO | WO 00/62781 A1 | 10/2000 | |
| WO | WO 01/80875 A1 * | 11/2001 | ............ 424/94.5 |

OTHER PUBLICATIONS

Osten et al., Protein Synthesis-Dependent Formation of Protein kinase M zeta in Long-Term Potentiation J. Neuroscience, Apr. 15, 1996, 16(8):2444-2451.*
Vianna et al., Pharmacological demonstration of the differentia involvement of Protein kinase C isoforms in short—and long-term memory formation and retrieval of one-trial avoidance in rats. Pysophamacology (2000) 150:77-84.*
Izquierdo et al., Separate mechanisms for short- and long—term memory. Behavioral Brain Research 103 (1999) 1-11.*
Quevedo et al., Protein synthesis, PKA, and MAP kinase are differentially involved in short- and long-term memory in rats. Behavioral Brain Research 154 (2004) 339-343.*
Drier, E.A., et al., "Enhancement of Memory in Drosophila Via Induction of a Mouse PKC Isoform MPKM-+B", *Society for Neuroscience Abstracts*, 26(1-2):94, Abs. 38.4 (2000).
Hrabetova, S., et al., "Bidirectional Regulation of Protein Kinase Mζ in the Maintenance of Long-Term Potentiation and Long-Term Depression", *Journal of Neuroscience*, 16(17):5324-5333 (1996).
Osten, P. et al., "Differential downregulation of protein kinase C isoforms in spreading depression", *Neuroscience Letters*, 221:37-40 (1996).
Barad, M., et al., Mice Overexpressing a Constitutively Active PKMζ Derived Transgene in Brain Under CAMKII Promoter Control Show Defects in Memory and Increased Incidence of Neurofibromas, *Society of Neuroscience Abstracts*, 24(1-2):328, Abs. 131.14 (1998).
Ebadi, M., et al., "Actions and Regulation of Protein Kinase C in Brain", *Neuroendocrinology Letters*, 15(1-2):69-88 (1993).
Drier, E.A., et al., "Memory Enhancement and Formation by Atypical PKM activity in *Drosophila melanogaster*," *Nature Neuroscience* 5(4): 316-324 (2002).
Sacktor, T.C., et al., "Persistent Activation of the Zeta Isoform of Protein Kinase C in the Maintenance of Long-term Potentiation," *Proc. Natl. Acad. Sci. USA* 90(18): 8342-8346 (1993).
Rubin, G.M., et al., "Comparative Genomics of the Eukaryotes," *Science* 287: 2204-2215 (2000).
Reiter, L.T., et al., "A Systemic Analysis of Human Disease-Associated Gene Sequences in *Drosophila melanogaster*," *Genome Res. 11*: 1114-1125 (2001).

* cited by examiner

*Primary Examiner*—Nashaat T. Nashed
*Assistant Examiner*—Kagnew Gebreyesus
(74) *Attorney, Agent, or Firm*—Hamilton, Brook, Smith & Reynolds, P.C.

(57) ABSTRACT

Methods have been developed for alleviating memory problems or psychiatric dysfunctions that have a memory formation component. These methods are based on the finding that a truncated form of an aPKCζ protein is intimately involved in memory formation in animals. This finding is also central to methods for determining drugs that will have an effect on memory formation or the memory formation component of psychiatric dysfunctions.

14 Claims, 11 Drawing Sheets

H   B 73 kD  ▬  ▬  DaPKC 47.5 kD  ▬  DaPKM

α-MaPKCζ
C-term. 16 aa

α-MaPKCζ
C-term. 16 aa

| 0 | 1 | 10 | 100 | 1000 | | 1000 |

590         545

DaPKC competing peptide

ALLEVIATION OF THE MEMORY DEFICITS AND MEMORY COMPONENTS OF PSYCHIATRIC DYSFUNCTIONS BY ALTERING ATYPICAL PKM ACTIVITY

RELATED APPLICATIONS

This application claims the benefit of U.S. Provisional Application No. 60/326,948, filed on Oct. 4, 2001, and also claims the benefit of U.S. Provisional Application No. 60/287,165, filed on Apr. 27, 2001.

The entire teachings of the above application(s) are incorporated herein by reference.

GOVERNMENT SUPPORT

The invention was supported, in whole or in part, by grants MH053576 and MH057068 from the National Institute of Mental Health. The Government has certain rights in the invention.

BACKGROUND OF THE INVENTION

Mental illnesses are significant for their debilitating effect on the individuals who suffer their manifestations. The rest of society is significantly affected since they must provide care for the individuals who are afflicted with these diseases. Mental impairments that result from such events as strokes are also significant for their adverse consequences for the individuals who suffer their debilitating effects. Memory deficits in individuals have major consequences for them and for others with whom they interact. Although much effort has been expended in an attempt to overcome these maladies, there remain large deficiencies in the ability to understand and effectively treat them. Further treatment modalities are constantly being sought. In particular, the biochemical bases for these diseases or states remains largely unknown and knowledge of these bases will foster further drug discoveries.

All of these diseases or states have a significant memory component. This is particularly true, obviously, when memory loss or abnormally poor memory is the prime or only symptom. Knowing biochemical molecules that centrally participate in memory will lead to methods and compositions that lessen memory abnormalities and will alleviate mental diseases or psychiatric dysfunctions by addressing the memory component of these diseases or dysfunctions.

SUMMARY OF THE INVENTION

The present invention is directed to methods of alleviating memory problems and psychiatric dysfunctions in mammals by modulating the expression, or activity, of a truncated form of an aPKC ZETA (aPKCζ) protein in the central nervous system of the mammal. A particular trucated form of the aPKCζ protein that is responsive to modulation is aPKMζ. Modulation of protein expression can be achieved by either induction or inhibition of formation of aPKMζ. Modulation of activity can be achieved by affecting interacting proteins that participate in the normal memory formation process. Memory problems include abnormal memory formation due to normal aging, injury to the brain, neurodegeneration, and Alzheimer's disease or other decreases in cognitive ability. The present invention alleviates memory deficits associated with these situations. In this instance, the problem is alleviated by inducing expression of aPKMζ and memory formation is particularly improved when the expression of aPKMζ is induced. Psychiatric dysfunctions for which alleviation can be achieved include attention deficit disorder, autism, fragile X syndrome, bipolar disorder, schizophrenia, obsessive compulsive disorders and phobias. In this regard, the psychiatric dysfunctions are alleviated by affecting or altering the memory formation component of the particular dysfunction.

The present invention is also directed to methods of identifying substances that can affect memory formation or psychiatric dysfunctions in mammals. In these methods, a substance under scrutiny is administered to a mammal. It is then determined whether the substance alters the expression or activity of aPKMζ protein in the central nervous system of the mammal when compared to the expression or activity of the same protein in the absence of the substance. If there is a difference in such expression or activity, and the aPKMζ protein is associated with a memory defect or a given psychiatric dysfunction, the substance affects that defect or dysfunction. The portion of the psychiatric dysfunction that is affected when the substance alters the expression or activity of the aPKMζ protein is the memory formation component of the dysfunction. In particular instances, an increase in expression or activity of the aPKMζ protein when the substance is administered is indicative that the substance will enhance the memory formation component of dysfunction. By contrast, a decrease in expression or activity of the aPKMζ protein when the substance is administered is indicative that the substance will interfere with the memory formation component of the dysfunction.

The present invention is further directed to methods for assessing the effect of a drug on regular memory disorders or the memory formation component of a psychiatric dysfunction. To test the effect of a drug on regular memory disorders, animal models for a memory disorder are trained and tested in the presence and absence of the drug. If the drug affects performance relative to the performance of animals that were trained identically but in a drug-free state, then the drug has an effect on regular memory disorders. Regular memory disorders result from the processes of normal aging, traumatic injury to the brain, Alzheimer's disease, and neurodegeneration. To test the effect of the drug on the memory formation component of a psychiatric dysfunction, the drug is administered to an animal that has an animal model for a specified psychiatric dysfunction. The animal is subjected to a training protocol and the performance index of the animal is assessed. The drug is found to have an effect on memory formation when the performance significantly differs between drug-free and drug-treated animals that were trained identically. Psychiatric dysfunctions which have a memory formation component and for which the effects of drugs can be assessed by these methods include attention deficit disorder, autism, Fragile X syndrome, bipolar disorder, schizophrenia, obsessive compulsive disorder and phobias.

The present invention is further directed to methods of alleviating regular memory disorders and psychiatric dysfunctions in mammals by modulating the expression of an aPKMζ gene that is associated with the regular memory disorder or the psychiatric dysfunction. When the modulation is induction of the aPKMζ gene, the induction enhances the normal memory formation process, or the memory formation component of a psychiatric dysfunction. Regular memory disorders result from normal aging, traumatic injury to the brain, Alzheimer's disease and neurodegeneration. Psychiatric dysfunctions for which alleviation can be achieved by modulation of an aPKMζ gene include attention deficit disorder, autism, Fragile X syndrome, bipolar disorder, schizophrenia, obsessive compulsive disorder, and phobias.

This peptide is derived from the C terminus of the DaPKC protein. The antiserum was made against the C terminus of MaPKMζ. which is homologous to the DaPKC protein. A peptide derived from an upstream region of DaPKC (545) does not compete with the immunoreactivity even at 1,000-fold excess.

Figures 6A, 6B:
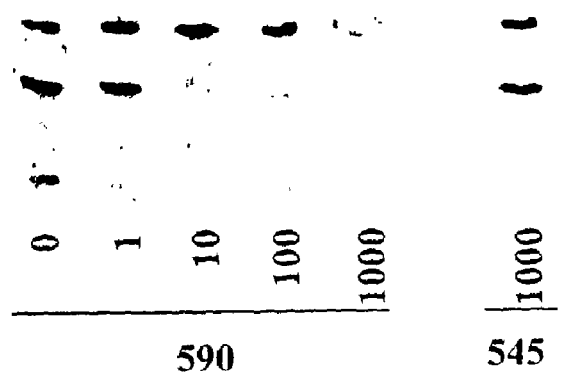
FIG. 6A. A *Drosophila* homolog of MaPKMζ is present and active in *Drosophila* head extracts. Antisera against MaPKC/Mζ detect DAPKC and DaPKM. Separate extracts from fly heads and bodies were analyzed on western blots using antisera directed against the C-terminal 16 amino acids of MaPKC/Mζ. The molecular weights of the two immunoreactive bands agree with those predicted for the DaPKC (73 kDa) and DaPKM (55 kDa) isoforms. The putative DaPKM is enriched in heads.
FIG. 6B. DaPKC and DaPKM immunoreactivity is competed with DaPKC-specific peptides. Western blots were done on head extracts. The antiserum was added along with 0, 1-, 10-, 100- or 1000-fold excess DaPKC-590 peptide.
Figure 6C:
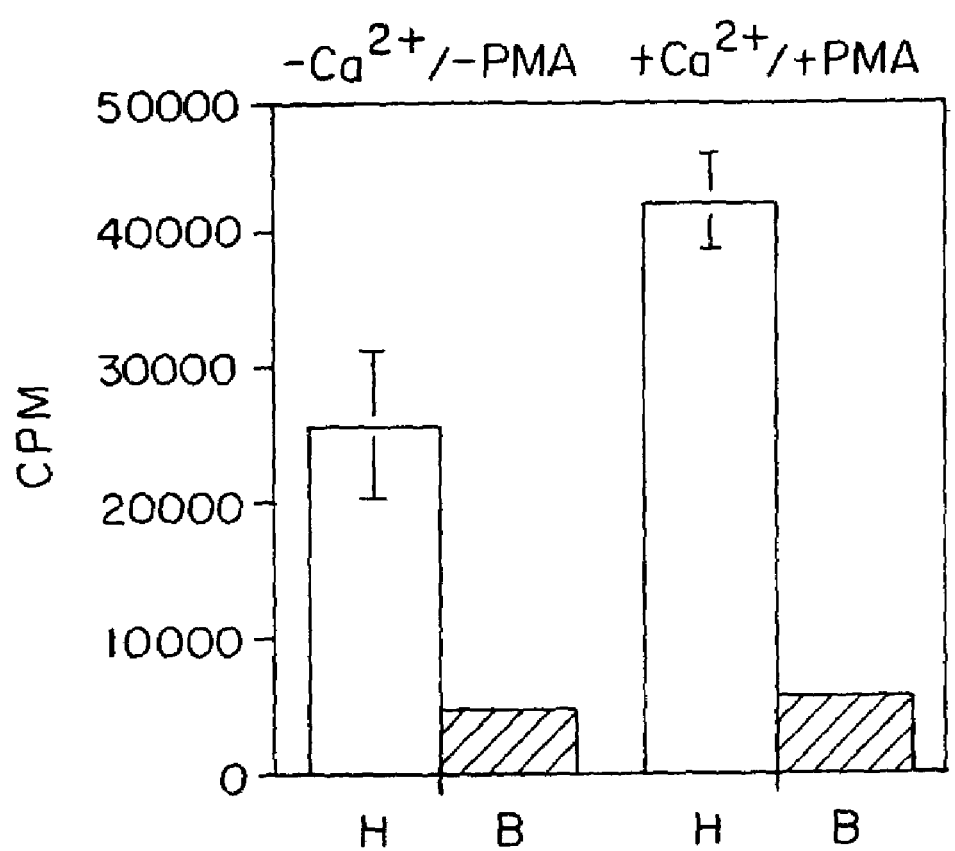

FIG. 6C. Atypical PKC activity is enriched in extracts made from *Drosophila* heads. Separate extracts were made from wild-type fly heads and bodies as in (a). They were assayed for aPKC activity as in FIG. 2b.

Figure 7A:
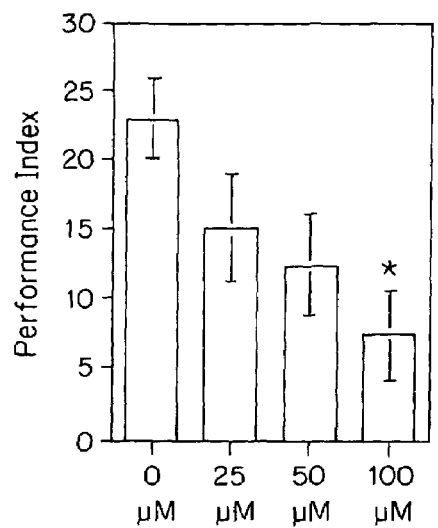

FIG. 7A. Chelerythrine treatment or KI-MaPKMζ expression inhibits 24-h memory produced by massed training, but not learning, in *Drosophila*. Chelerythrine inhibits 24-h memory after massed training in a dose-dependent manner. Wild-type flies were fed either sucrose (0 μM) or 25 μM, 50 μM or 100 μM chelerythrine in a sucrose solution. They were given three cycles of massed training and assessed for 24-h memory. n=8 for all groups.

Figure 7B:
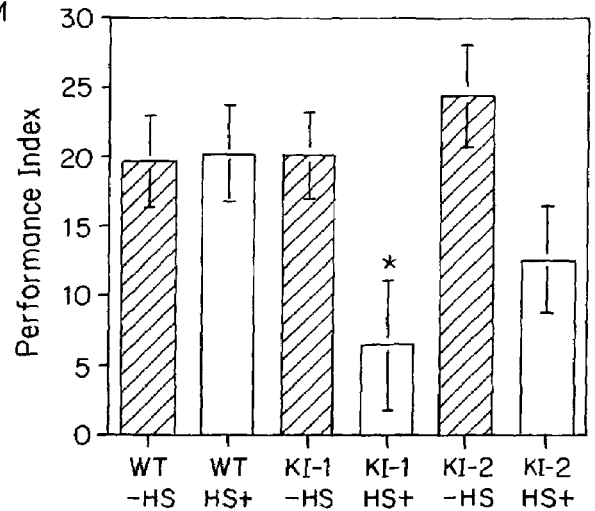

FIG. 7B. The KI-MaPKMζ mutant inhibits 24 h memory produced by massed training. Each line of the hsp70-KI-MaPKMζtransgene (KI-1 and KI-2) was induced with a 30-min, 37° C. heat shock, allowed to recover for 3 h at 25° C., and then given 10 cycles of massed training. Line KI-1 induction caused a significant reduction in 24-h memory, and induced KI-1 flies were also significantly different from induced control flies (WT, HS+). Line KI-2 induction also seems to reduce memory, but this line may not be as effective as KI-1. n=8 for all groups.

Figure 7C:
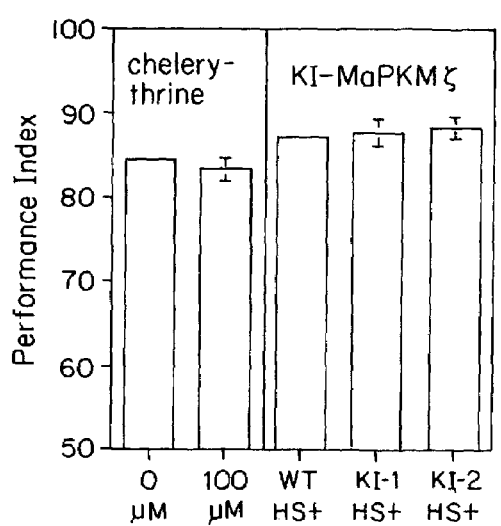

FIG. 7C. Neither chelerythrine nor KI-MaPKMζ induction affects learning. After a 1-h starvation period, wild-type flies were fed either sucrose (0 μM) or 100 μM chelerythrine in a sucrose solution for 3 h. The KI-MAPKMζ was induced as in (b). In both cases. the flies were then given single-cycle training and tested immediately after training to assess learning. There was no difference between relevant groups: sucrose-fed flies were not different from chelerythrine-fed flies, and WT HS+flies were not different from KI-1 HS+or KI-2 HS+flies. n=8 for all groups.

Figure 8A:
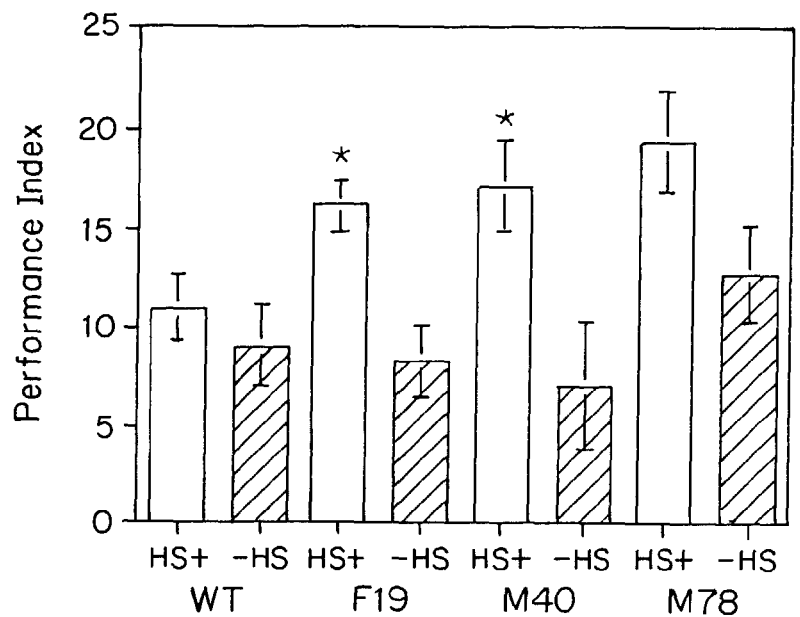

FIG. 8A DaPKM induction enhances memory. DAPKM enhances 24-h memory after single-cycle training. Flies were given single-cycle training, allowed to recover at 25° C. for 30 min, and the DaPKM transgene was induced by a 32° C. heat shock lasting 30 min. Performance was measured 24 h later. Three independent transgenic lines were tested (FI9, M40, and M78). n=8 for all groups. The asterisks indicate significant differences.

Figure 8B:
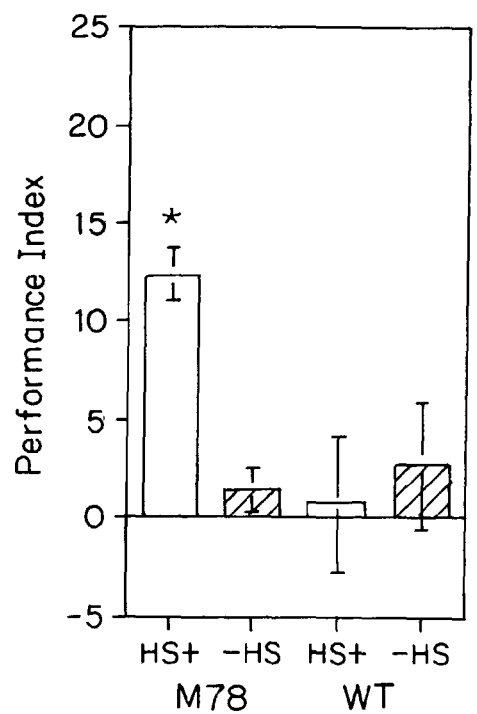

FIG. 8B. DaPKM enhances 4-day memory after massed training. DaPKM-M78 flies were trained with 10 cycles of massed training, allowed to recover for 30 min at 25° C., and induced as in (a). Performance was measured at 4 days; n=8 for all groups. Only line M78 was used for this analysis, and it shows significant induction-dependent improvement of 4-day memory.

Figure 8C:
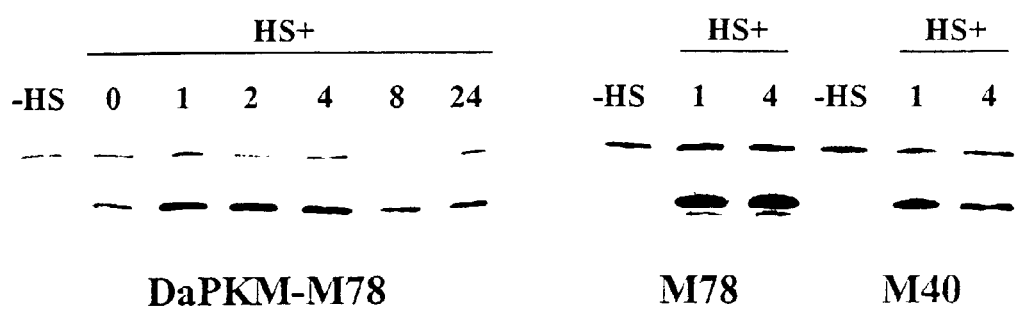

FIG. 8C. Western blot analyses of DaPKM induction after heat-shock. Flies were subjected to heat shock (32° C.) for 30 min. Left, time-course western blots of the DaPKM-M78 line. At the indicated time points, flies were collected and head extracts were used for western blot analysis. All times are relative to the end of the heat-shock treatment. Right, direct comparison of the induction of the M40 and M78 lines. In both panels, the upper band is a background band included as a load-control reference.

DETAILED DESCRIPTION OF THE INVENTION

This invention relates to methods of alleviating memory problems and psychiatric dysfunctions in mammals, particularly in humans, by modulating the expression or activity of a truncated form of an aPKCζ protein in the central nervous system of the mammal. The expression of the truncated form of the aPKCζ protein is modulated by affecting molecular processes of transcription, mRNA stability, protein stability, proteolytic processing, and translation initiation. The activity of the protein is modulated by post-translational modifications on the protein, protein:protein interactions, and subcellular localization of the protein.

Modulation of expression occurs when the amount of the truncated form of the aPKCζ protein differs from the amount that is present without modulation. There can be an increase in the amount of truncated form of the aPKCζ protein, decrease in the amount of truncated form of the aPKCζ protein, or a variation over a defined time span of an increase and/or a decrease in the amount of truncated form of the aPKCζ protein. For example, the amount of truncated form of the aPKCζ protein can increase in a linear or nonlinear fashion over time, decrease in a linear or nonlinear fashion, or alternatively increase and decrease, linearly or nonlinearly. An increase in the amount of the truncated form of the aPKCζ protein, or in the amount of an inhibiting form of the protein, in a linear or nonlinear fashion, is generally preferred for the alleviation of psychiatric dysfunctions.

The protein that is formed by the expression process in this invention is a truncated form of an aPKCζ protein. This protein is produced either by synthesis of the full-length protein, followed by proteolytic processing, or de novo synthesis of the truncated form of the protein, aPKMζ. This de novo synthesis may occur from transcription initiation sites located in intronic regions of the gene, and/or translation initiation from internal methionine codons.

Modulation of the expression of the truncated form of an aPKCζ protein can occur either by an induction or by an inhibition of the expression of the truncated form. When induction of expression occurs, more of the truncated form is produced than when this induction is not present. When inhibition of expression occurs, less of the truncated form is produced than when this inhibition is not present. Under certain conditions, a given amount of the truncated form of the aPKCζ protein normally may be produced. Under these conditions, induction of expression increases the amount of the truncated form that is produced and inhibition of expression decreases the amount of the truncated form that is produced from this given amount. In these instances, modulation of the expression of the truncated form causes an increase, decrease, or alternative increase and decrease, linearly or nonlinearly, from the given amount that is normally present.

In this invention, the preferred truncated form of the aPKCζ protein is aPKMζ. This is the truncated form of the a typical isozyme PKCζ that lacks the N-terminal regulatory domain of the PKCζ protein. The N-terminal regulatory domain contains a pseudosubstrate region as well as binding sites for the required cofactors. The aPKMζ, which lacks this N-terminal regulatory domain, contains the C-terminal catalytic domain and is a persistently active kinase derived from the aPKCζ isozyme. Induction of the expression of aPKMζ protein or inhibition of the expression of the aPKMζ protein are preferred in this invention to alleviate psychiatric disorders. Of these, induction of expression is most preferred.

Normal memory problems can be alleviated by modulating the expression or activity of aPKMζ. These memory problems can result from normal aging, traumatic injury to the brain, Alzheimer's disease and neurodegeneration. Classical memory disorders include loss or lack of ability to recall specific past experiences or events. The loss or lack of ability to make proper or normal associations between these prior events or past experiences is also included in these disorders. These disorders also include the loss or lack of ability to make proper or normal associations between prior events or past experiences and present cognitive functions or experiences. Short term memory loss and long term memory loss are particular memory deficits that are included in these disorders. Short term memory losses are the loss or lack of ability to recall or make correct or proper associations between present perceptions and recent events or experiences. Long term memory losses are the loss or lack of ability to recall or make correct or proper associations between present perceptions and events or experiences that were perceived some time ago by the individual. The distinction between short term memory and long term memory varies with the animal species, behavioral task, and training regimen, and is generally known to people to whom this distinction is important. For all animals, long-term memory is the memory phase whose induction is sensitive to protein synthesis inhibitors given acutely around the time of training. Short-term memory are all phases of memory that are resistant to such inhibitors. Generally, short term memories last from minutes, to hours and a few days after training, while long-term memories persist for longer periods of time.

Many memory problems and psychiatric dysfunctions can be alleviated by modulating the expression of aPKMζ in animals. Alleviation of a given psychiatric dysfunction occurs when the symptoms of the dysfunction are lessened and the individual exhibits more normal behavior patterns and modes. In certain instances, and usually desired, alleviation of a given psychiatric dysfunction is essentially complete and the individual exhibits normal behavior. In rare instances, the individual exhibits normal behavior traits before the expression of aPKMζ protein is modulated. Under these circumstances, better than normal behavior is sought and expression of the truncated form is modulated to achieve this result.

Among the memory problems that can be alleviated by modulating the expression of aPKMζ are those resulting from normal aging, injury to the brain, Alzheimer's disease or neurodegeneration. Among the psychiatric dysfunctions that can be alleviated by modulating the expression of aPKMζ are attention deficit disorder, autism, fragile X syndrome, bipolar disorder, schizophrenia, obsessive compulsive disorder, and phobias.

In the present invention, memory is affected by modulation of expression of the aPKMζ protein. Depending upon the protein isoform that is modulated, memories can be enhanced or blocked. The aPKMζ appears to have a noticeable effect on short term memory when its expression is modulated. Short term memory improves when expression of aPKMζ is induced.

Without being bound by any mechanism of action, it appears that the psychiatric dysfunctions that are alleviated by modulating the expression of a truncated form of aPKMζ in the central nervous system of the animal are aided or relieved because the modulation affects the memory formation component of the psychiatric dysfunction. By making the appropriate changes to the memory formation component, the symptoms of the psychiatric dysfunction are lessened and the psychiatric dysfunction is altered in a favorable manner. In many instances, it is the short term memory component of the psychiatric dysfunctions that is affected by modulating the expression of the APKMζ protein. Induction of expression of the aPKMζ causes an enhancement of the short term memory component of the psychiatric dysfunction. Inhibition of expression or activity of aPKMζ causes an interference with the short term memory component of the psychiatric dysfunction. Either an enhancement or interference with the short term memory component can alleviate a given psychiatric dysfunction. Whichever process is desired to alleviate the psychiatric dysfunction will be employed. For example, when an individual exhibits a lack or loss of short term memory ability, the expression of aPKMC can be induced to relieve symptomology.

The amount of truncated form of aPKCζ protein in the central nervous system of the animal can be changed or modulated in a variety of manners. Transcription of the endogenous gene can be modulated. Any small molecule or physiological stimulus that affects the amounts or activity of the different transcription factors that modulate gene expression will affect levels of the mRNA and protein. Alternatively, DNA based manipulations can be performed to change the regulation of the endogenous gene. Exogenous regulatory sequences can be added to the endogenous gene, putting the gene under the control of different DNA sequences, proteins that bind those sequences, and effectors that affect those proteins. In these situations, modulation of expression of the truncated form occurs when the effector is administered from an external source or withheld, depending on the action that occurs at the regulation site.

Another manner of changing or modulating the amount of aPKMζ protein in the central nervous system of the animal is using transgenic technology. A transgene that encodes a desired aPKMζ protein is inserted into the genome of the animal. The transgene can be inserted using recombinant techniques recognized and known to skilled persons such as molecular biologists. The transgenic animal can contain one or more copies of the transgene that encodes the truncated form of the aPKMζ protein. This transgene may contain the endogenous gene. More likely, the transgene encodes a selected aPKMζ protein of another animal species. In either instance, the transgene can be under the control of either endogenous regulation sites or regulation sites obtained from exogenous sources. Endogenous regulation sites can be employed when the transgene is inserted at an appropriate locus in the genome where gene expression is controlled by the endogenous regulation site. However, regulation sites from exogenous sources are more often employed when transgenes are used. The regulation sites are often easier to include with the transgenes when the genome insertions are performed. In either situation, the inserted transgene encoding the desired aPKMζ provides more control of the modulation, particularly induction, of the expression of the truncated form. This increased control enhances the ability to alleviate memory defects and psychiatric dysfunctions.

A further manner of changing the amount of aPKMζ protein in an individual is by administration of the protein itself to the individual. The protein is administered so that it is active in the central nervous system of the individual and thereby alleviates the memory defect or psychiatric dysfunction by altering the memory formation component of the dysfunction. This protein can be an active or inhibitory form of the molecule.

This invention also relates to methods of identifying substances that affect memory formation or psychiatric dysfunctions in mammals, particularly in humans. The substance usually has an organic chemical structure and is in the form of a pharmaceutical with the required diluents, excipients and carriers present in its formulation. The substance may be a macromolecule but usually it is much smaller. In these methods, the substance under consideration is administered to a mammal. The administration is by any standard route. For example, administration can occur by oral or rectal intake, inhalation, topical application, or parenterally by subcutaneous, intravenous or intramuscular injection. Once administered, it is determined whether the substance alters the expression or activity of an aPKMζ protein in the central nervous system of the mammal, where it has previously been shown that the aPKMζ protein is associated with the psychiatric dysfunction of interest. The association of the aPKMζ protein and the psychiatric dysfunction can be direct or indirect. The association is present if an alteration in the amount or activity of the aPKMζ protein either enhances or diminishes the signs or symptoms of the psychiatric dysfunction. The association is present if an alteration in the genetic expression of the aPKMζ protein either enhances or diminishes the signs or symptoms of the psychiatric dysfunction. Alteration of expression or activity of the aPKMζ protein is determined by comparing the expression or activity of this protein after the substance is administered to the mammal with the expression of the protein when the substance has not been administered. If a reproducible difference is found between the expression or activity values for the aPKMζ protein when the substance is present versus when the substance is not present, the substance is identified as having the property of affecting the psychiatric dysfunction with which the aPKMζ protein is associated. The substance can be further identified as having an alleviating or a deleterious effect on the psychiatric dysfunction, depending on the relationship of the expression change with the quality or intensity of the signs or symptoms of the psychiatric dysfunction. For example, if an increase in the expression or activity of the aPKMζ protein is associated with an alleviation of the signs or symptoms of the psychiatric dysfunction and the substance, when administered, causes an increase in the expression or activity of the aPKMζ protein, the substance is considered to have advantageous properties for alleviating the psychiatric dysfunction.

Often for aPKMζ, when the administered substance causes an increase in the expression or activity of the APKMζ, the substance is considered to have the property of enhancing the memory formation component of the psychiatric dysfunction. Often, it is the short term memory component of the psychiatric dysfunction that is enhanced when the administered substance causes an increase in the expression of aPKMζ. Conversely, when the administered substance causes a decrease in the expression or activity of the aPKMζ, the substance is considered to have the property of interfering with the memory formation component of the psychiatric dysfunction. In this instance, it is again often the short term memory formation component of the psychiatric dysfunction that is interfered with or blocked by the administered substance.

This invention further relates to methods for assessing the effects of drugs on the memory formation component of psychiatric dysfunction. In these methods, the candidate drug is administered to a normal animal or an animal that possesses an inducible aPKMζ protein which is associated with memory formation. The drug usually has an organic chemical structure and is administered by any of the standard administration routes together with any required diluents, excipients or carriers. In these methods, the animal type is not limited to mammals but includes most of the animal kingdom. For example, insects such as *Drosophila melanogaster* or honeybees can be used as subjects for assessing the effects of drugs on the memory formation component. Other model organisms for assessing drug effects on memory formation include *C. elegans*, Aplysia, Xenopus, zebrafish, mouse, rats, ferrets and cats. The only requirement for animal type is that it have an inducible truncated form of an aPKCζ protein which is associated with memory formation.

Following the administration of the candidate drug to the animal in these methods, the inducible aPKMζ protein is induced to produce the truncated form in the animal, or the endogenous gene is examined in the nontransgenic animal. Induction can be performed by any of the methods known to persons who are familiar with such processes. In *C. elegans*, practitioners usually use heat-shock, antibiotics or small molecules such as IPTG. In *Drosophila*, practitioners usually use heat-shock, antibiotics, or small molecules like IPTG or heavy metals. In mammals, practitioners usually use antibiotics, hormones or small molecules like IPTG.

After the expression of the aPKMζ protein has been induced in the transgenic animal, or the endogenous gene in the normal animal, the animal is subjected to a learning and memory assay, and a performance index, based on the outcome of the protocol, is assigned. Learning and memory tests are known to psychologists and others who study learning and memory in animals. The training protocols that are useful in this invention address learning and memory attributes which the animal possesses. Any discriminative classical conditioning protocol can be used. Exemplary of these protocols are associative and non-associative conditioning protocols, classical and operant conditioning, and tests of implicit and explicit memory. The performance index is an assessment of the results of the training protocol that was used. Often the performance index is a numerical value that is assigned by the observer or investigator to the outcome of the training protocol. The numerical value can be considered to be a scaled score for the performance of the animal undergoing the classical conditioning protocol.

In these methods, the drug is considered to have an effect on memory formation or the memory formation component of the psychiatric dysfunction when animals treated with the compound reproducibly perform differently from untreated animals. In some instances, the same individual animal may serve as the control animal and the one to whom the drug is administered. Usually, however, different animals serve as the untreated (control) and treated (subject) animals. In these instances, the animals should be chosen from the same cohort. The drugs that exhibit an effect on the memory formation component, as detected by these methods, are candidates for administration to animals to alleviate psychiatric dysfunctions in these animals, particularly when the psychiatric dysfunction has a memory formation component.

In these methods, the inducible target of the drug is aPKMζ. In these instances, it is typically the short term memory formation component of the memory problem or psychiatric dysfunction that is affected by the drug. Memory problems targeted by the selected drugs include those resulting from normal aging, injury to the brain, Alzheimer's disease and neurodegeneration. Psychiatric dysfunctions for which the drugs selected by these methods will have an effect include attention deficit disorder, autism, fragile X syndrome, bipolar disorder, schizophrenia, obsessive compulsive disorders, and phobias.

The study of PKC in memory formation has a long history. However, most previous studies were done before the complexity of the PKC gene family was appreciated. The PKC family can be divided into three classes based on their cofactor requirements. Whereas all PKC proteins require phosphatidylserine for activation, the 'conventional' (cPKC) isotypes require diacylglycerol (DAG) and Ca2+ for full activity; 'novel' (nPKC) isotypes are Ca2+ independent but still require DAG, and the 'atypical' (aPKC) isotypes are both DAG and Ca2+ independent. Structurally, these kinases can be divided into an N-terminal regulatory domain, which contains a pseudosubstrate region as well as the binding sites for the required cofactors, and the C-terminal catalytic domain. Removal of the N-terminal regulatory domain produces a persistently active kinase, referred to as PKM.

The roles of PKC in hippocampal models of synaptic plasticity, long-term potentiation (LTP), and long-term depression (LTD) have been studied extensively (see, F. Angenstein, et al., *Prog. Neuropsychopharmacol. Biol. Psychiatry* 21, 427-454 (1997)). Western blot analyses with antibodies specific for each of the rat PKC isoforms demonstrate that the only one whose levels specifically increase and remain elevated during the maintenance phase of LTP is PKMζ, the truncated form of the a typical isozyme PKCζ (see, e.g., Osten, P. et al., *J Neurosci.* 16, 2404-2451 (1996)). Expression analyses also show that the maintenance of LTD is associated with decreasing levels of PKMζ. Most interestingly, LTP maintenance is abolished by sustained application of low concentrations of the PKC inhibitor chelerythrine, whereas perfusion of PKMζ into CA1 pyramidal cells produces an increase in AMPA receptor-mediated synaptic transmission (D. S. F. Ling et al, unpublished data).

In *Drosophila*, the best characterized assay for associative learning and memory is an odor-avoidance behavioral task (T. Tully, et al. *J. Comp. Physiol.* A157, 263-277 (1985) incorporated herein by reference). This classical (Pavlovian) conditioning involves exposing the flies to two odors (the conditioned stimuli, or CS), one at a time, in succession. During one of these odor exposures (the CS+), the flies are simultaneously subjected to electric shock (the unconditioned stimulus, or US), whereas exposure to the other odor (the CS−) lacks this negative reinforcement. Following training, the flies are then placed at a 'choice point', where the odors come from opposite directions, and expected to decide which odor to avoid. By convention, learning is defined as the fly's performance when testing occurs immediately after training. A single training trial produces strong learning: a typical response is that >90% of the flies avoid the CS+. Performance of wild-type flies from this single-cycle training decays over a roughly 24-hour period until flies once again distribute evenly between the two odors. Flies can also form long-lasting associative olfactory memories, but normally this requires repetitive training regimens.

This task in *Drosophila* was used to examine in an exemplary fashion herein the role of atypical PKM in memory formation. Induction of the mouse aPKMζ (MaPKMζ) transgene enhances memory, and corrects the memory defect of radish mutants. There is a single atypical PKC in *Drosophila*, and the truncated 'M' isoform, DaPKM, was found to be preferentially expressed and active in fly heads. Both pharmacological and dominant-negative genetic intervention of DaPKC/M activity disrupt normal memory. Finally, induction of the predicted DaPKM also enhances memory, further demonstrating a general role of aPKM in memory processes.

A description of preferred embodiments of the invention follows.

EXEMPLIFICATIONS

Methods

Fly Stocks and Maintenance.

The background stock (2202 u) used as wild-type flies in all the experiments is w (isoCJ1), which is an isogenic line derived from a $w^{1118}$line backcrossed repeatedly to a Canton-S wildtype strain. To minimize differences in genetic background, 2202 u also served as the recipient strain for all of the transgenic lines used in these experiments. Fly stocks used for behavioral analyses were maintained under appropriate conditions.

Pavlovian learning and memory in *Drosophila*. To assess learning and memory in *Drosophila*, an olfactory-avoidance classical (Pavlovian) conditioning protocol was used. This protocol was modified to facilitate automated and repetitive training regimens. 3-octanol (OCT) and 4-methylcyclohexanol (MCH) were used as odors in these experiments. Detailed descriptions of single-cycle massed and spaced training as well as testing and the tests for olfactory acuity and shock reactivity can be found in Tully et al., *Cell* 79, 35-47 (1994) or Connolly, J. B. & Tully T., *Drosophila: A Practical Approach* (ed. Roberts, D. B., Oxford Univ. Press, Oxford 1998) incorporated herein by reference. The performance index (PI) was calculated by subtracting the number of flies making the incorrect choice from those making the correct one, dividing by the total number of flies, and multiplying by 100. To avoid odor-avoidance biases, the PI of each single n was calculated by taking an average performance of two groups of flies, one group trained with the CS+ being OCT, the other with the CS+ being MCH.

Transgenes

The MaPKMζ DNA construct was produced using PCR amplification using the full-length, MaPKCζ cDNA (American Type Culture Collection (ATCC) no.63247) as the template. PCR primers (upstream primer: 5'-CTAGCGAAT-TCAACATGAAGCT GCTGGTCCATAAACG-3' (SEQ ID NO. 1); downstream primer: 5'-CTAGCTCTAG ATCA-CACGG ACTCCTCAGC-3' SEQ ID NO. 2) were used to produce the truncated MaPKMζ gene. The upstream primer contained an EcoRI restriction site just 5'of a consensus Kozak sequence and also encoded an ATG start codon. The last 20 nucleotides of the upstream primer correspond to 20 nucleotides in the hinge region of the MaPKCζ gene. The second codon in this truncated gene corresponds to amino acid 165 in the MaPKCζ protein. The downstream primer is antisense to the last 20 nucleotides in the MaPKCζ open reading frame, and contains a XbaI restriction enzyme site immediately after the translation stop codon. The PCR product produced using these primers was cut with EcoRI and XbaI, then subcloned into a heat-shock P-element vector, using the same restriction sites, and sequenced. The kinase-inactive KI-MaPKMζ was produced in the same manner except that the K281W-MaPKCζ mutant DNA was used as the template for PCR amplification. The full-length MaPKCζ gene was subcloned into the same P-element vector using the EcoRI sites located at both ends of the cDNA and in the heat-shock vector. Transgenic flies were made using standard techniques. Based on homology with mammalian PKCζs, the N terminus of DaPKC was defined as beginning with residues M-P-S. Using this reference point, the DaPKM transgene begins at Met223 within the hinge region of DaPKC.

Heat-Shock Induction

All fly stocks were maintained at 25° C. before and after heat-shock. Heat-shock inductions were performed in 15-ml plastic tubes (~100 flies/tube) by partially submerging the tubes in a waterbath at the appropriate temperature (32° C. or 37° C.) for 30 min.

Biochemical Assay

MaPKMζ transgenic flies maintained at 25° C. were heat-shocked at 37° C. for 30 min, then allowed to recover at 25° C. for 1 h and frozen in liquid nitrogen. Uninduced controls and wild-type flies remained at 25° C. throughout. After freezing, fly heads were separated from bodies and ~100 μl of heads were homogenized in 1 ml extraction buffer (20 mM Hepes pH 7.4, 0.2 M sucrose, 1 mM EDTA, 1 mM EGTA, 1 mM phenylmethylsulfonyl fluoride (PMSF), and Complete protease inhibitor cocktail (Roche, Indianapolis, Ind.)), and centrifuged at 176,500 g for 10 min. The homogenates were diluted to 1 mg/ml protein and adjusted to 2.5 mM EGTA. PKC activity was assayed by measuring the incorporation of $^{32}P$ from $\gamma$-$^{32}P$-ATP into peptide-ε (Peninsula, Belmont, Calif.). Each 50-μl reaction contained 50 mM Hepes pH 7.4, 10 mM $MgCl_2$, 1 nM dithiothreitol (DTT), 25 μM peptide-ε, 20 μg of protein homogenate, and 20 mM $\gamma$-$^{32}P$-ATP (2 μCi). The protein was incubated at 26° C. for 1 min in the reaction mixture lacking ATP. The reaction was started by the addition of $\gamma$-$^{32}P$-ATP, incubated at 26° C. for 2 min and stopped on ice with 20 μl of 75 mM $H_3PO_4$. A 20-μl aliquot from each reaction was spotted onto a 2-cm circle of P81 chromatography paper (GIBCO, Gaithersburg, Md.) and washed three times in 75 mM $H_3PO_4$ dried, and the radioactivity measured by scintillation counting. The effect of Ca2+ and phorbol esters in the reaction was measured in the presence of 200 μM $CaCl_2$ and 400 μM phorbol myristate acetate (PMA). Background activity was estimated from mock reactions lacking peptide-ε. PKC activity increased linearly with time up to 4 min. The values reported are averages from quadruplicate assays.

Western Blots

The heat-shock induction time course was monitored using fly-head extracts (approximately five heads per lane were loaded) for the western analyses. A rabbit polyclonal antibody against MaPKMζ (Sigma, St. Louis, Mo.) was used as the primary antibody, and the protein was detected using ECL (Pierce, Rockford, Ill.).

Chelerythrine Feeding

A 4% (wt/vol) sucrose solution was used as a vehicle for the chelerythrine feeding. Onto Whatman 3MM filter paper cut to fit and placed in the bottom of standard fly culture vials, 120 μl of 0 μM (sucrose alone), or 25 μM, 50 μM or 100 μM chelerythrine was applied. Flies were starved in empty vials (~100 flies/vial) for 1 h, and then transferred to the feeding vials for 3 h to allow sufficient feeding. Flies were then trained and tested as described in the text and figures. Feeding was monitored by placing 1/50 volume of green food coloring into the solutions, which could then be seen in the abdomens of flies after eating. There was no noticeable difference in consumption between any of the solutions.

Results

MaPKMζ Induction Enhances Memory in *Drosophila*

Figure 1A:
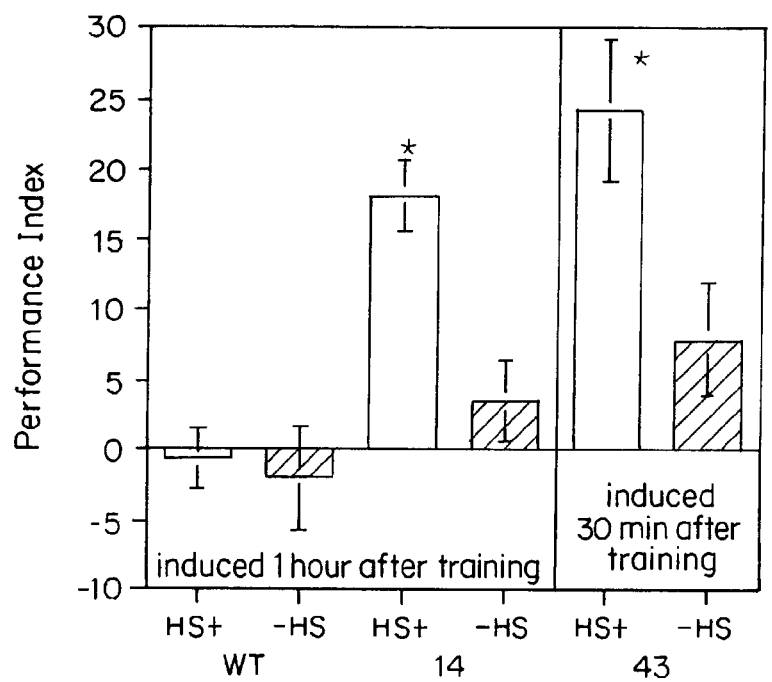
FIG. 1A Memory enhancement by MaPKMζ in *Drosophila*. Memory enhancement by heat-shock induction after training of two independent lines bearing a hsp 70-MaPKMζtransgene. Flies were subjected to single-cycle training, allowed to recover at 25° C., and the MaPKMζ transgene was induced with a 30-min, 32° C. heat shock. Performance was measured 24 h later. The induction of line 14 and the wild-type (WT) control began 1 h after training ended, and the induction of line 43 began 30 min after training. Both lines show clear induction effects (n=8 for all groups). Error bars represent standard error of the mean and, unless noted, the asterisks indicate statistical significance calculated using ANOVA and Dunnet's test throughout this work.

To investigate the role of PKC in learning and memory in *Drosophila*, transgenic lines of flies were made bearing heat shock-inducible murine a typical PKC (MaPKC) isoforms. Considering that LTP experiments indicate that MaPKMζ levels increase after the presentation of the stimuli required for long-lasting potentiation, inducing MaPKMζ after training was tested to see if it affected olfactory memory. Induction by mild heat shock (32° C.) after training strongly enhanced 24-hour memory (FIG. 1a). This enhancement was not due to transgene-independent heat-shock effects, because the wild-type flies did not show enhanced memory when exposed to heat shock. The transgenic flies were made in this wild-type strain, so the enhancement was not due to differences in genetic background. Finally, the memory enhancement did not result from an insertional mutation caused by the transgene, because two independent lines (MaPKMζ-14 and MaPKMζ-43) had similar effects.

Figure 1B:
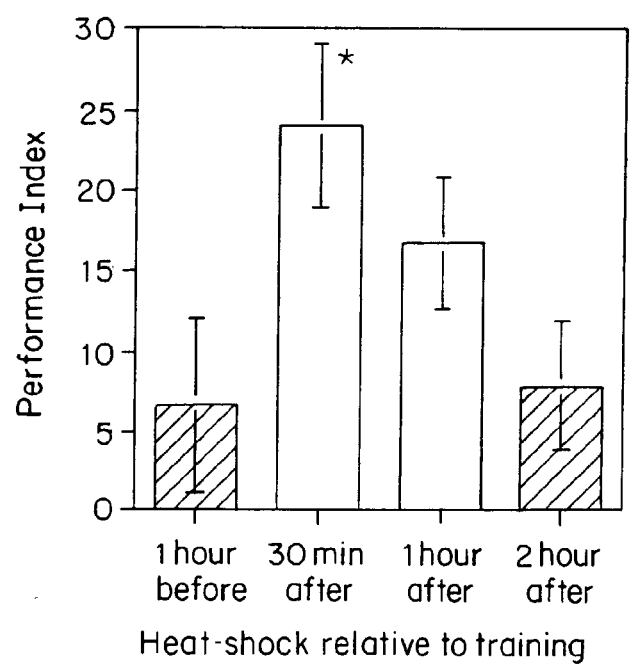
FIG. 1B. Temporal specificity of the memory enhancement by MaPKMζ. MaPKMζ transgenic flies (line 14) were subjected to a 30-min, 25-32° C. heat shock at various times before and after a single cycle of training, and tested for 24-h memory. Histograms from left to right: heat shock ended 1 h before, 30 min after, 1 h after or 2 h after training began; heat shock began 30 min, 1 h after or 2 h after training ended, respectively, n=8 for all groups.

Enhancement of 24-hour memory after single-cycle training by inducing MaPKMζ with a strong heat shock (37° C.) 3 hours before training was also tested, but this regimen had no effect (data not shown). Because transgene induction after behavioral training enhanced memory, whereas induction before training did not, the temporal specificity of this MaPKMζ dependent effect was next examined. Optimal enhancement was found to occur when heat-shock induction begins 30 minutes after training ends, and the effect is absent if heat shock occurs before, or is delayed until 2 hours after training (FIG. 1b).

Figure 2A:
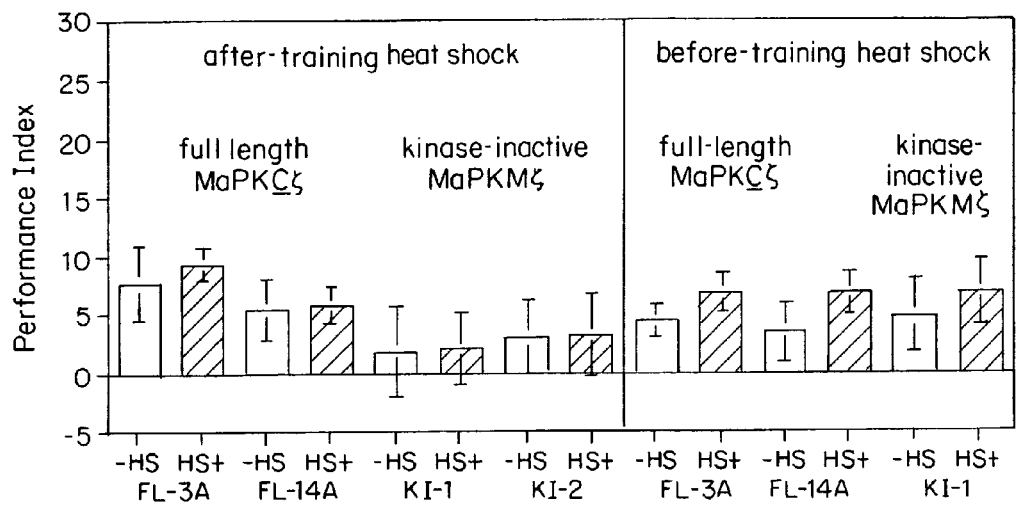
FIG. 2A. Memory enhancement requires persistent kinase activity and is not due to sensory enhancement. Neither a kinase-inactive (KI) mutant of MaPKMζ nor full-length (FL) MaPKMζ enhances 24-h memory. Two independent lines (FL-3A, FL-14A) of the full-length hsp70-MaPKMζtransgene (Methods) and two independent lines (KI-1 and KI-2) of a hsp70-KI-MaPKMζtransgene were assessed for memory enhancement. The KI-MaPKMζ mutant (K281W) disrupts kinase activity by altering the ATP-binding domain. Two different heat-shock schedules were used: a 30-min, 32° C. induction 3 h before training, or a 30-min, 32° C. heat shock given 30 min after the end of training. Neither heat-shock regimen produced induction-dependent enhancement of 24-h memory in any of these lines.

The memory enhancement was not observed when a kinase-inactive (KI) mutant of MaPKMζ was induced either before or after training (FIG. 2a; two independent lines, KI-1 and KI-2, of KI-MaPKMζ). The enhancement was also not observed when full-length (FL)-MaPKCζ was induced before or after training (FIG. 2a; two independent lines, FL-3A and FL-14A). The failure of either the KJ-MaPKMζ or the FL-MaP-KCζ transgene to enhance memory was not due to lack of expression, because both are expressed at levels comparable to the MaPKMζ protein (FIG. 3a; KI-1 and FL-14A versus MaPKMζ-14). Together, these results indicate that the memory enhancement (FIG. 1) requires a persistently active aPKM isoform.

Biochemical Detection of MaPKMζ Induction in *Drosophila*

Figure 3A:
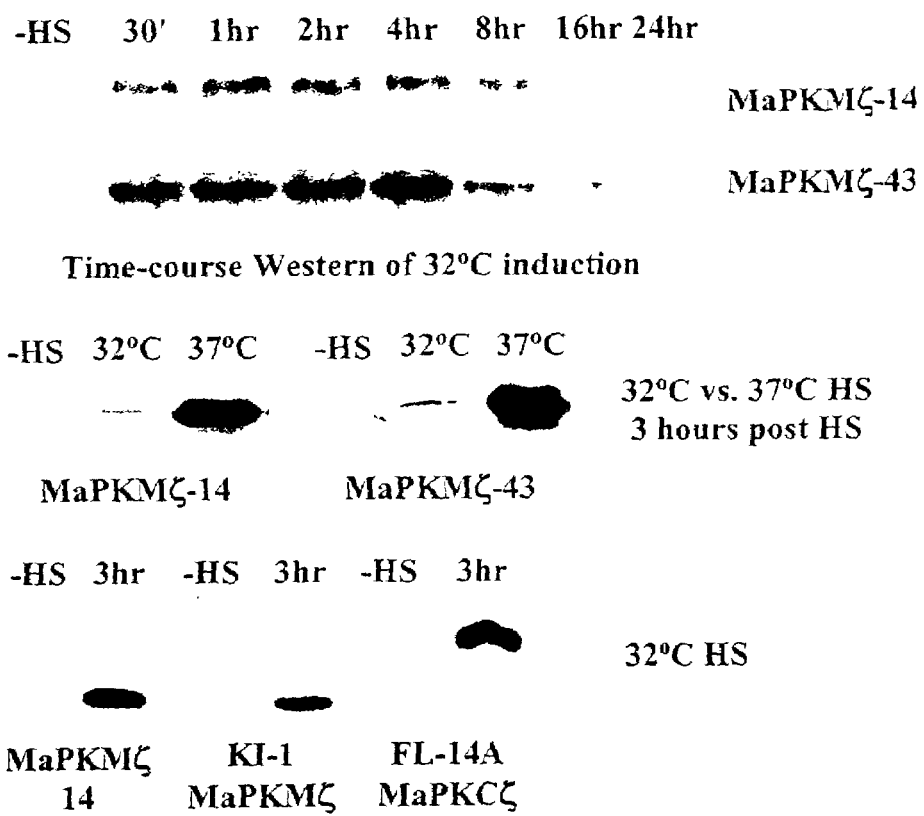
FIG. 3A. Expression and biochemical analyses of transgenic lines. Western blot analyses of MaPKMζ and MaPKCζ induction after heat shock. Flies were subjected to heat shock (32° C. or 37° C.) for 30 min. Top, time-course western blots from both MaPKMζ lines. At the indicated time points, flies were collected and head extracts were used for western blot analysis. Middle, direct comparison of the induction achieved at 32° C. versus 37° C. In each case, the flies were heat-shocked for 30 min, and head extracts were made after 3 h of recovery time. Bottom, direct comparison of the expression of the MaPKMζ (line 14), the kinase-inactive (KI)-MaPKMζ (KI-1), and full-length (FL)-MaPKCζ (FL-14A). For each western blot, equivalent amounts of total protein (five heads per lane) were loaded in each lane.
Figure 3B:
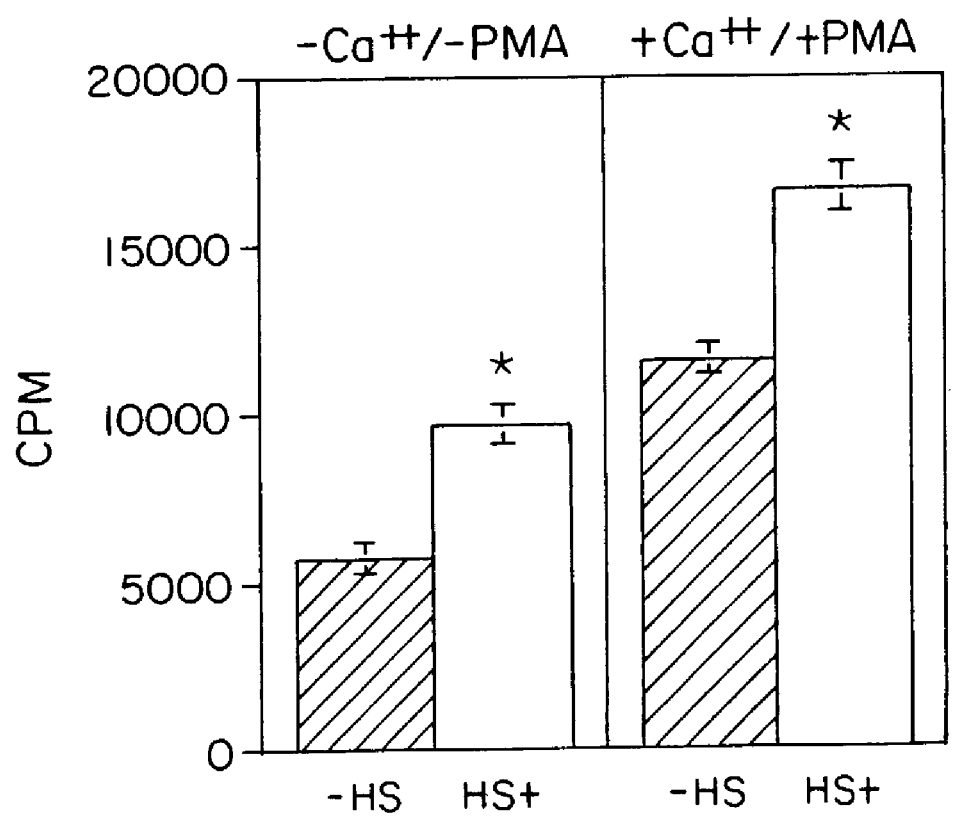
FIG. 3B. Expression and biochemical analyses of transgenic lines. Induction of MaPKMζ results in an increase in a typical PKC activity in fly head extracts. MaPKMζ transgenic flies (line 43) were subjected to a 37° C. heat shock for 30 min, allowed to recover at 25° C. for 1 h, and frozen in liquid nitrogen. Control flies remained at 25° C. throughout. Total protein extracts were made from fly heads and assayed for PKC activity. An increase in kinase activity could be detected ($-Ca^{2+}/-PMA$: HS+versus −HS, p=0.0057, n=4; $+Ca^{2+}/+PMA$: HS+versus —HS, p=0.0011, n=4: Student's t-test) with a strong (37° C.) but not with a mild (32° C.) heat shock (data not shown). The induction levels are much greater at 37° C. versus 32° C. (a).

Inducible increases in MaPKMζ protein levels and kinase activity were detected in extracts made from *Drosophila* heads (FIG. 3). Western blot analyses showed that both the mild and strong heat-shock regimens induced the MaPKMζ and MaPKCζ isoforms, and that these proteins persisted for ~18 hours after heat shock (FIG. 3a). The induced MaPKMζ protein was active, as indicated by an observed enhancement of $Ca^{2+}$/DAG(diacylglycerol)-independent PKC activity in fly head extracts from induced but not from uninduced transgenic flies (FIG. 3b).

MaPKMζ Induction Does Not Affect Peripheral Behaviors

Figure 2B:
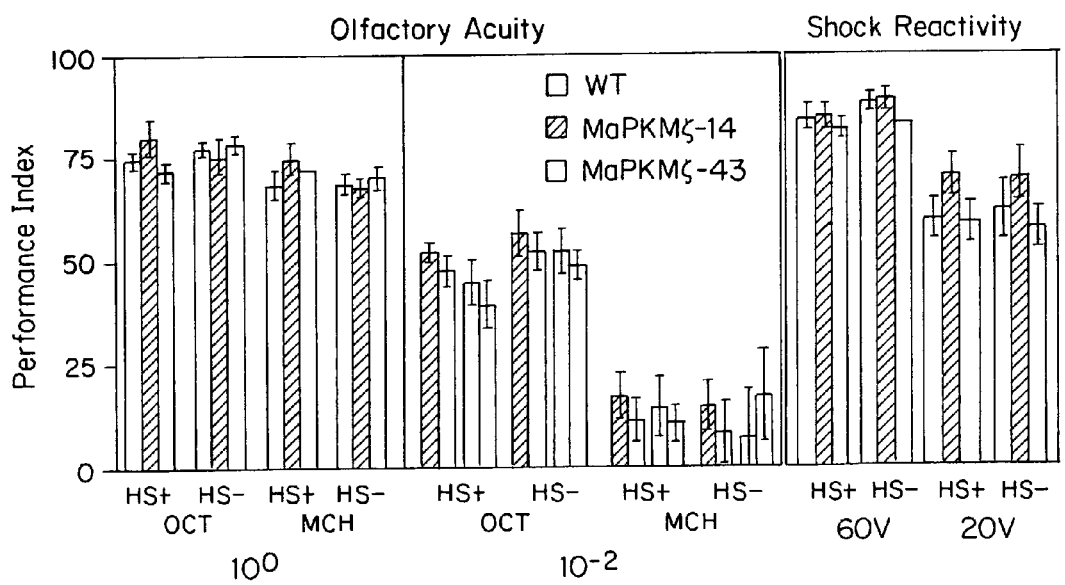
FIG. 2B. Memory enhancement requires persistent kinase activity and is not due to sensory enhancement. Induction of MaPKMζ does not affect peripheral behaviors. Flies were subjected to a 30-min, 32° C. heat shock. allowed to recover for 1 h, then tested for shock reactivity. Olfactory acuity was tested by exposing the flies to a 30-min, 32° C. heat shock, and assayed for odor acuity 24 h later. The legend inset in the olfactory acuity panel applies to both sets of histograms. In all measures, both the MaPKMζ lines (14 and 43) were indistinguishable from the wild-type controls. The most critical control is the $10^{-2}$ olfactory acuity test, and for this the transgenic flies were heat-shocked (or not), stored, and tested simultaneously with their respective wild-type controls. Both sets of wild-type controls, adjacent to their transgenic counterparts, were included for direct comparison.

The memory enhancement occurred only when the transgene was induced after training; therefore it is not likely due to an effect of transgene expression on the perception of either the shock or the odors at the time of training. No effect of MaPKMζ induction on shock reactivity was found, as the transgenic flies behaved indistinguishably from the wild-type strain, irrespective of heat shock (FIG. 2b). Thus, transgenic flies did not perceive shock better during training. Because the memory enhancement was induction-dependent (FIG. 1a), it cannot be attributed to small amounts of leaky expression during training. Although MAPKMζ had decayed to pre-heat-shock levels by the time of testing at 24 hours (FIG. 3a), enhancement of olfactory responses at the time of testing by MaPKMζ could be occurring. However, this was not the case because olfactory acuity at 24 hours after induction was normal (FIG. 2b). These data demonstrate that the MaPKMζ induction has no behavioral effect on either sensory modality, and indicate that the effect observed is due to bona fide memory enhancement.

MaPKMζ Enhances Memory After Massed, but not Spaced Training

Drosophila can form associative olfactory memories lasting 24 hours and longer, but this normally requires repetitive training. Multiple-trial training regimens have been established that produce both anesthesia-resistant memory (ARM) and long-term memory (LTM). ARM can be produced by 10 cycles of 'massed' training with no rest intervals between the individual training trials, and lasts 2-3 days. LTM results from repetitive training that contain rest intervals (15 min each; see Methods), and 10 cycles of this 'spaced' training generates LTM that lasts at least 7 days. To test whether MaPKMζ could enhance ARM or LTM, flies were subjected to massed or spaced training regimens, the transgene was induced for 30 minutes after training, and then 4-day memory was measured.

Figure 4A:
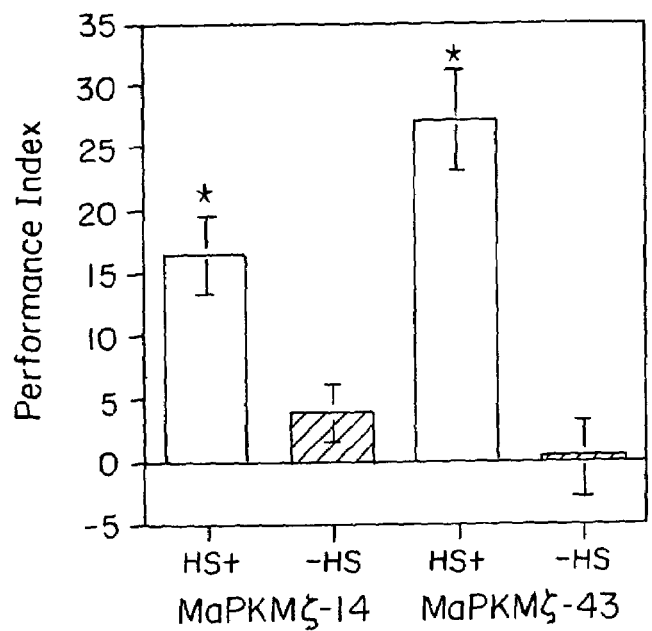
FIG. 4A. MaPKMζ induction enhances 4-day memory after massed, but not spaced training. MaPKMζ induction after massed training enhances 4-day memory. MaPKMζ flies were trained with 10 cycles of massed training, allowed to rest for 30 min, then subjected to a 30-min heat shock (32° C.). Performance was measured at 4 days; n=8 for all groups. Both lines (14 and 43) show significant induction-dependent improvement of 4-day memory. At 4 days, the memory induced by massed training has normally decayed so that the PI=0, as is the case for uninduced flies (-HS).

MaPKMζ induction substantially increased 4-day memory after massed training (FIG. 4a; HS+ compared to −HS for each line) but did not improve 4-day memory after spaced training (FIG. 4b; HS+ compared to −HS for each line). These data indicate that MaPKMζ induction enhances massed training-induced, but not spaced training-induced memory.

The Radish Mutation Does Not Block MaPKMζ-Induced Memory Enhancement

Previous work indicated that consolidated memory in Drosophila consists of two biochemically separable components: ARM and LTM. ARM is produced by either massed or spaced training, and it is insensitive to cycloheximide treatment. LTM is produced by spaced training and is blocked by cycloheximide treatment; thus it is considered to require acute protein synthesis. A previously identified Drosophila memory mutant, radish, is deficient in ARM, as this mutation blocks memory produced by massed training. Spaced training of radish mutants does produce memory, but this memory can be completely blocked by treating the mutants with cycloheximide. These results led to a two-pathway model of consolidated memory, one dependent on the radish gene product (ARM) and the other dependent on activity-induced, acute protein synthesis (LTM). (See Tully et al, Cell 79, 35-47 (1994).

Figure 5:
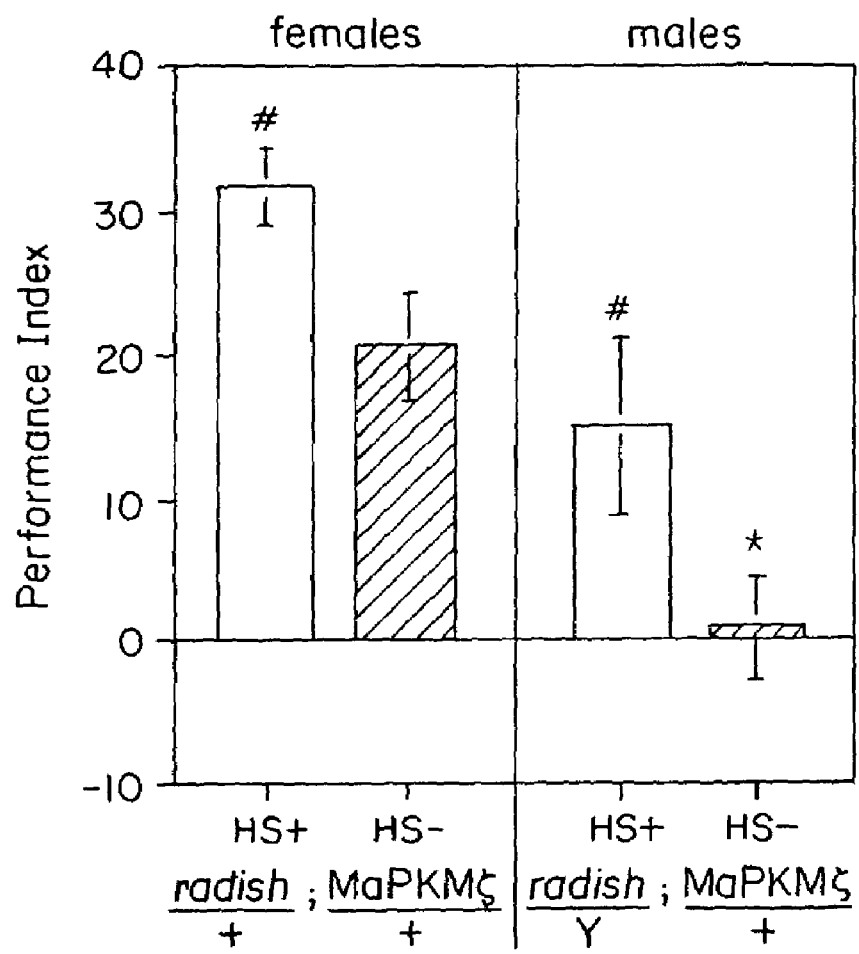
FIG. 5. MaPKMζ induction corrects the memory deficit of radish mutants. Homozygous radish females were mated to males homozygous for an autosomal MaPKMζ transgene. (Line 43 was used in this experiment.) Male and female progeny from this mating were trained and tested together, providing an internal control, and then counted separately to generate sex-specific PI values. The genotypes of the males and females are give below the histogram. Using Dunnet's test with uninduced females as the control group, the only group showing statistically different performance is the uninduced males (noted by the asterisk). Analysis of HS+versus HS− groups using Student's t-test shows that both males and females display significant differences in performance by transgene induction (denoted by #).

Because MaPKMζ induction enhanced memory after massed but not after spaced training, the dependence of this effect on radish was tested. The radish gene is on the X chromosome in Drosophila and homozygous radish mutant females were crossed to males homozygous for an autosomal copy of the heat shock-inducible MaPKMζ transgene. The radish mutant is recessive, thus the heterozygous female progeny of this mating will have normal memory after massed training, whereas the hemizygous males will display the radish memory deficit in the absence of induction. The progeny were subjected to massed training, followed by the standard MAPKMζ induction after training, and then tested at 24 hours to assess the ability of MaPKMζ. Males and females were trained and tested en masse and then separated and counted. The radish mutation did not block the memory effect of MaPKMζ induction (FIG. 5). The memory defect of radish males was apparent in the absence of heat-shock induction (HS−), but memory was clearly present in induced males (HS+). A lesser, but significant induction-dependent memory enhancement of the heterozygous radish females by MAPKMζ was also observed (FIG. 5: HS+versus HS− females).

A Drosophila Homolog of MaPKMζ

There is a single atypical PKC (DaPKC) gene in the Drosophila genome, and it is highly homologous to the MaPKCζ gene used. (The kinase domain shows 76% identity and 87% similarity.) A western blot of extracts made from wild-type fly heads and bodies showed that the antiserum used to detect MaPKMζ and MaPKCζ recognized two bands in fly extracts, the smaller of which was enriched in head extracts (FIG. 6a). This antiserum is directed against the C-terminal 16 amino acids of MaPKC/Mζ, which shares substantial homology with DaPKC. Antiserum from mice immunized with peptides derived from DaPKC recognized these same bands (data not shown). The molecular weights of these two bands indicate that they are probably the DaPKC (~73 kDa) and DaPKM (~55 kDa) isoforms.

We have not established the N-terminal sequence of the lower molecular weight band; however, it likely represents an endogenous DaPKM isoform. The immunoreactivity was competitively reduced by a peptide from the corresponding region of DaPKC, but not one outside of this epitope (FIG. 6b, 590 and 545, respectively) or by a peptide from another Drosophila protein (dCREB2, data not shown). In agreement with the western blot data, fly heads contained more Ca2+ and DAG-independent PKC activity than did bodies (FIG. 6c). The presence of the putative DaPKM correlates strongly with this enriched activity, suggesting that most, if not all, of the endogenous a typical kinase activity we measured in head extracts was due to this DaPKM isoform. These data indicate that flies possess both 'C' and 'M' forms of an a typical PKC that is highly homologous to MaPKC/M, and that the DaPKM is enriched in heads.

Chelerythrine and KI-MaPKMζ Inhibit Memory, but not Learning

A P-element insertional mutant in DaPKC has been described; however, it is an embryonic lethal and thus is not suitable for examining a possible role in adult learning and memory formation. To assess whether this gene's product is necessary for memory formation, two approaches were taken. First, the effects on memory of feeding flies the PKC inhibitor chelerythrine were monitored. This drug is reported to selectively inhibit PKMζ at low concentrations (D. S. F. Ling et al., unpublished data and Laudanna, C. et al, J. Biol. Chem. 273, 30306-30315 (1998); however, its specificity is controversial, and it inhibits other PKC isotypes at higher concentrations. Measurements were also made of memory effects produced by inducing the kinase-inactive KI-MaPKMζ protein, which displays 'dominant-negative' activity that is likely to be specific to the a typical PKCs, leaving cPKC and nPKC responses intact.

Feeding flies chelerythrine inhibited 24-hour memory formation in a dose-dependent manner (FIG. 7a), and induction of the KI-MaPKMζ inhibited 24-hour memory after massed training (FIG. 7b). The inhibitory effects of both chelerythrine and the KI-MaPKMζ were not likely due to effects on olfactory acuity or shock reactivity because learning was unaffected by either treatment (FIG. 7c).

DaPKM Induction Enhances Memory

The memory enhancement produced by MaPKMζ could have been due to properties unique to this mammalian protein. The expression data showing that DaPKM was expressed and active in Drosophila heads, when combined with the chelerythrine and dominant-negative data, suggested that DaPKM is involved in normal memory processes in Drosophila. The extensive structural homology between MaPKMζ and DaPKM also argued against functional uniqueness. An hypothesis of functional homology makes a strong prediction: induction of DaPKM after training should also enhance memory.

Using as a basis the approximate molecular weight of the DaPKM, the DAPKC gene was truncated within the hinge region separating the regulatory from the catalytic domains such that the putative DaPKM gene begins at methionine 223. Induction of the DaPKM transgene after training enhanced 24 hour memory after single-cycle training (FIG. 8a). One of these lines was used to show that 4-day memory after massed training was also enhanced (FIG. 8b). As with the MaPKMζ transgenes, the DaPKM lines showed rapid heat-shock induction (FIG. 8c). These results confirm those obtained with MaPKMζ, and thus indicate that aPKM is fundamental in the mechanisms underlying memory across species.

Discussion of Results

Atypical PKM and Normal Memory

These results provide strong evidence that a typical PKM activity is sufficient to enhance memory in Drosophila. Both pharmacological and dominant-negative interventions were investigated. Chelerythrine inhibited normal memory in a dose-dependent manner (FIG. 7a), and induction of a predicted dominant-negative a typical PKM produced the same memory deficit (FIG. 7b).

It is important to note that neither of the employed inhibitory interventions disrupted learning (FIG. 7c). Screens in Drosophila have identified many learning mutants that disrupt several signaling pathways (e.g., cAMP-PKA, integrin-mediated, and 14-3-3 protein-dependent processes; for original citations). Considering that learning remains normal, it is unlikely that either intervention produced very broad signaling defects. With this in mind, the observation that each intervention inhibited memory without disrupting learning indicates that DaPKC/M is a component of an endogenous memory mechanism.

Phase Specificity of MaPKMζ-Enhanced Memory

Figure 4B:
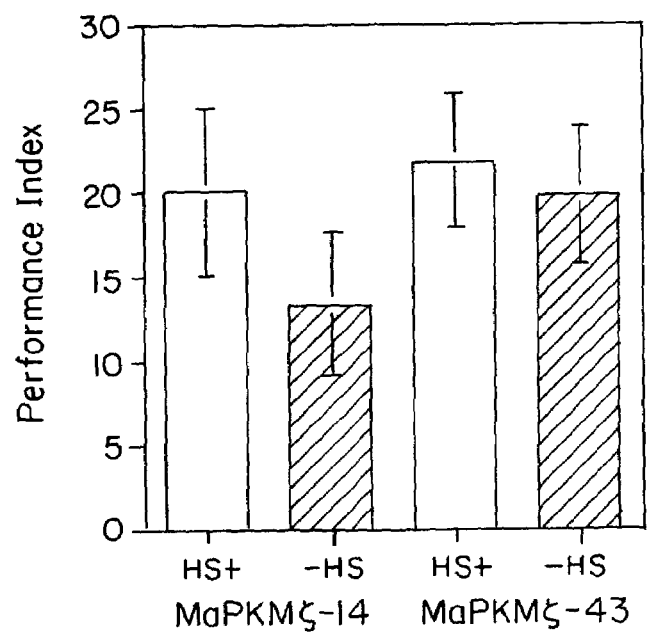
FIG. 4B. Four-day memory produced by spaced training is not improved by MaPKMζ induction. MaPKMζ flies were trained with 10 cycles of spaced training (Methods), allowed to rest for 30 min, and subjected to a 30-min, 32° C. heat shock. Memory was measured 4 days after training. n=8 for all groups. Neither line shows a significant effect of transgene induction on memory after spaced training. To rule out an effect of saturation, flies were also trained with a submaximal number of spaced trials (7), but transgene induction still had no effect (data not shown).

Heat-shock induction of MaPKMζ did not enhance long-term memory, because it did not improve memory after spaced training (FIG. 4b). One explanation for this is that spaced training induces endogenous maintenance mechanisms, and thus occludes the effect of inducing the MaPKMζ transgene. Thus, memory after single-cycle or massed training may be prolonged by transgene induction because these training regimens do not normally induce prolonged a typical PKM activity. Work in honeybees showed that single-cycle training produces neither persistent PKC activity nor long-lasting memory, but multiple-cycle training produces both (see L. Grunbaum et al, J. Neurosci. 18, 4384-4392 (1998)). The memory enhancement observed when inducing MaPKMζ may simply bypass the endogenous requirements (normally provided by spaced training) for prolonged activation of aPKM.

The MaPKMζ-induced enhancement of massed, but not spaced training prompted an examination the involvement of the radish gene product in this process. If radish were required for the enhancement, the radish mutation would have blocked the MAPKMζ-induced effect, and this was clearly not the case (FIG. 5). Although MaPKMζ induction phenotypically rescues the memory defect of radish, it does not do so because radish encodes for the Drosophila aPKM. DaPKM is on the second chromosome and radish is on the X, and no Drosophila PKC gene maps to the genetically defined radish locus. There are two principal possibilities explaining how MaPKMζ-induced memory enhancement bypasses the defect of radish mutants: (1) MaPKMζ is downstream of radish; (2) MaPKMζ activates a pathway that is parallel to and independent of radish. The first interpretation is favored because either enhancement or disruption of memory after massed training, as well as partial rescue of the radish phenotype can be carried out.

Atypical PKM and activity-dependent synaptic plasticity. There are two general interpretations of these data: PKMζ acts to increase either (1) the magnitude or (2) the duration of the synaptic potentiation that underlies the behavior. In the first model, PKMζ enhances the synaptic machinery induced by training, making a 'stronger' synaptic connection that decays more slowly. In the second model, PKMζ acts solely to maintain the synapses previously modified by experience, with no effect on the induction of the potentiation. If one considers the behavioral measurements of learning (testing done immediately after training) and memory (testing done after a longer time) with induction and maintenance, respectively, the chelerythrine and dominant-negative data argue for a role in maintenance. Neither of these treatments affected learning (FIG. 7c), but each inhibited memory (FIG. 7a and b). An enhancement of learning by prior induction of PKMζ was not detected (data not shown), nor was there an improvement of 3-hour memory if PKMζ was induced 30 minutes after training (data not shown). Although the magnitude and duration models may be artificially exclusive, taken together the data are most consistent with a role of PKMζ in the maintenance of experience-dependent synaptic plasticity.

The stability of a synapse varies in response to different regimens of stimuli. Long-lasting changes normally require multiple stimuli and depend on new protein synthesis. Recent experiments support the existence of a synaptic marking system that enables neurons to tag recently active synapses, thus maintaining synaptic specificity during the cell-wide process of protein synthesis-dependent long-term memory formation (see, e.g., U. Frey et al., Nature 385, 533-536 (1997)). A synapse that would normally be stable for only a short period of time can be potentiated for a much longer period of time. However, to do so it must be activated within 2-4 hours of stimulation that produces long-term changes at a second and separate synapse within the same neuron. Although no direct evidence for a role of PKMζ in this process was shown by these results, the similarity between the temporal windows for the proposed synaptic tag and the memory enhancement observed here suggest a mechanistic relationship between them.

DaPKC is part of a multiprotein complex important for both cell polarity and the asymmetrical cell divisions of early Drosophila neurogenesis (see, e.g., A. Wodarz et al, J. Cell Biol. 50, 1361-1374 (2000)). These processes show strong structural and functional parallels with the first asymmetrical cell division of Caenorhabditis elegans embryogenesis. The Drosophila homologs of C. elegans proteins important for this process, Par-3 (Bazooka) and Par-6 (Dm-Par-6), interact with each other and with DaPKC to direct a specific and interdependent subcellular localization of the complex. During early Drosophila embryogenesis, Bazooka, DmPar-6, and DaPKC are localized to the zonula adherens, a cell junction structure. Mutation in any one of these genes disrupts the ability of the remaining two proteins to localize to this structure properly, and this disrupts cell polarity. This mutual dependence for localization is also apparent during neurogenesis, and causes the inappropriate segregation of cell determinants. This multiprotein complex is critical in mammalian cell polarity and in organizing junctions between epithelial cells. The mouse homologs of Bazooka and Par-6 are expressed in various regions of the CNS, and their subcellular localization within CA1 hippocampal neurons is consistent with a role in synaptic plasticity (see D. Lin et al, *Nature Cell Biol.* 2, 540-547 (2000)). Bazooka and DmPar-6 are expressed in *Drosophila* heads, as are DaPKC and DaPKM (FIG. 6a).

Atypical PKM has been shown here to be sufficient to enhance memory in *Drosophila*, and the chelerythrine and dominant-negative data suggest that it is also necessary for normal memory.

While this invention has been particularly shown and described with references to preferred embodiments thereof, it will be understood by those skilled in the art that various changes in form and details may be made therein without departing from the scope of the invention encompassed by the appended claims.

present, compared to the expression or activity of said aPKMζ when said substance is not present, is indicative of an interference in normal memory formation or the memory formation component of said psychiatric dysfunction.

3. The method of claim 1 wherein an increase in the expression or activity of said aPKMζ when said substance is present, compared to the expression or activity of said aPKMζ when said substance is not present, is indicative of an enhancement of memory formation of said memory problem or the memory formation component of said psychiatric dysfunction.

4. The method of claim 1 wherein said substance alters the expression or activity of an aPKMζ protein in the central nervous system of said mammal by modulating either the induction of formation of an aPKMζ protein in the central

What is claimed is:

1. A method of identifying a substance that affects a short term memory problem or a short term memory formation component of a psychiatric dysfunction associated with atypical PKM zeta (aPKMζ) protein in a mammal, comprising:
   (a) administering said substance to a mammalian animal model; and
   (b) determining whether said substance alters the expression or activity of an aPKMζ protein in the central nervous system of said mammalian animal model when compared to the expression or activity of said aPKMζ protein in the absence of said substance;
   wherein a change in the expression or activity of said aPKMζ in the presence of said substance, compared to the expression or activity of said aPKMζ in the absence of said substance, is indicative that said substance affects short term memory formation or said short term memory formation component of said psychiatric dysfunction.

2. The method of claim 1 wherein a decrease in the expression or activity of said aPKMζ when said substance is nervous system of said mammal or the inhibition of formation of an aPKMζ protein in the central nervous system of said mammal.

5. A method of identifying a substance that affects a short term memory problem or a short term memory formation component of a psychiatric dysfunction associated with atypical PKM zeta (aPKMζ) protein in a murine mammal, comprising:
   (a) administering said substance to said murine mammal;
   (b) determining whether said substance alters the expression or activity of an aPKMζ protein in the central nervous system of said murine mammal when compared to the expression or activity of said aPKMζ protein in the absence of said substance;
   wherein a change in the expression or activity of said aPKMζ in the presence of said substance, compared to the expression or activity of said aPKMζ in the absence of said substance, is indicative that said substance affects short term memory formation or said short term memory formation component of said psychiatric dysfunction.

6. The method of claim 5 wherein the murine mammal is a mouse.

7. The method of claim 5 wherein the murine mammal is a rat.

8. The method of claim 5 wherein a decrease in the expression or activity of said aPKMζ when said substance is present, compared to the expression or activity of said aPKMζ when said substance is not present, is indicative of an interference in normal memory formation or the memory formation component of said psychiatric dysfunction.

9. The method of claim 5 wherein an increase in the expression or activity of said aPKMζ when said substance is present, compared to the expression or activity of said aPKMζ when said substance is not present, is indicative of an enhancement of memory formation of said memory problem or the memory formation component of said psychiatric dysfunction.

10. The method of claim 5 wherein said substance alters the expression or activity of an aPKMζ protein in the central nervous system of said mammal by modulating either the induction of formation of an aPKMζ protein in the central nervous system of said mammal or the inhibition of formation of an aPKMζ protein in the central nervous system of said mammal.

11. The method of claim 1, wherein whether said substance alters the expression of an aPKMζ protein in the central nervous system of said mammalian animal is determined.

12. The method of claim 1, wherein whether said substance alters the activity of an aPKMζ protein in the central nervous system of said mammalian animal is determined.

13. The method of claim 5, wherein whether said substance alters the expression of an aPKMζ protein in the central nervous system of said murine mammal is determined.

14. The method of claim 5, wherein whether said substance alters the activity of an aPKMζ protein in the central nervous system of said murine mammal is determined.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: PCR Primer

<400> SEQUENCE: 1
ctagcgaatt caacatgaag ctgctggtcc ataaacg                           37

<210> SEQ ID NO 2
<211> LENGTH: 29
<212> TYPE: DNA
<213> ORGANISM: Artificial Sequence
<220> FEATURE:
<223> OTHER INFORMATION: PCR Primer

<400> SEQUENCE: 2
ctagctctag atcacacgga ctcctcagc                                    29
```